US00PP11051P

United States Patent [19]

Heims

[11] Patent Number: Plant 11,051

[45] Date of Patent: Sep. 7, 1999

[54] TIARELLA PLANT NAMED 'CYGNET'

[75] Inventor: Dan M. Heims, Portland, Oreg.

[73] Assignee: Terra Nova Nurseries, Inc., Tigard, Oreg.

[21] Appl. No.: 09/002,959

[22] Filed: Jan. 6, 1998

[51] Int. Cl.[6] ..... A01H 5/00

[52] U.S. Cl. ..... Plt./263

[58] Field of Search ..... Plt./263

*Primary Examiner*—Howard J. Locker

*Assistant Examiner*—Melissa L. Kimball

*Attorney, Agent, or Firm*—Klarquist Sparkman Campbell Leigh & Whinston, LLP

[57] ABSTRACT

A new and distinct hybrid of Tiarella plant characterized by unique, heavily lobed leaves of marked coloration and heavy flowering.

2 Drawing Sheets

The present invention relates to a new and distinct hybrid of Tiarella which originated as a cross-pollination of *Tiarella cordifolia* 'Dunvegan' and a selected seedling of *Tiarella wherryi* in the Saxifrage family, both unpatented cultivars.

The new Tiarella is a result of a controlled cross of the aforementioned plants at Terra-Nova Nurseries, Inc., in Portland, Oreg. This hybrid was selected from a large selection of seedlings. Mother plants were retained to observe habit and to compare with their progeny. The new variety has been reproduced only by asexual propagation (division and tissue culture). Each of the progeny exhibits identical characteristics to the original plant and is unlike any Tiarella offered by any American nursery or book known to me as evidenced by the following characteristics:

1. Unique form and foliage shape

Asexual propagation by division and tissue-culture as done in Canby, Oreg., shows that the forgoing characteristics and distinctions come true to form and are established and transmitted through succeeding propagations.

Figure 1:
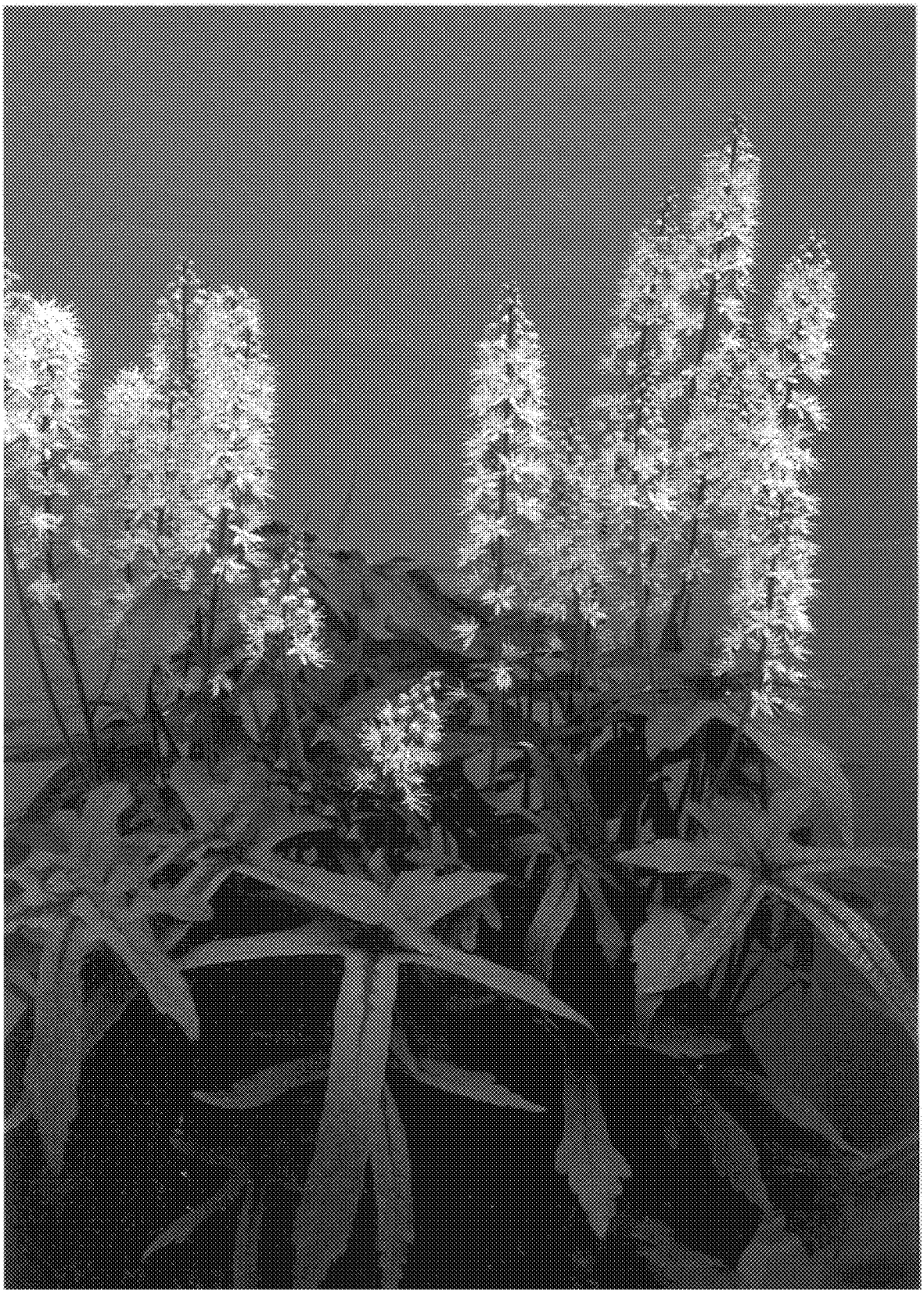

BRIEF DESCRIPTION OF THE PHOTOGRAPHS:

FIG. 1 is a picture of Tiarella 'Cygnet' in bloom.

Figure 2:
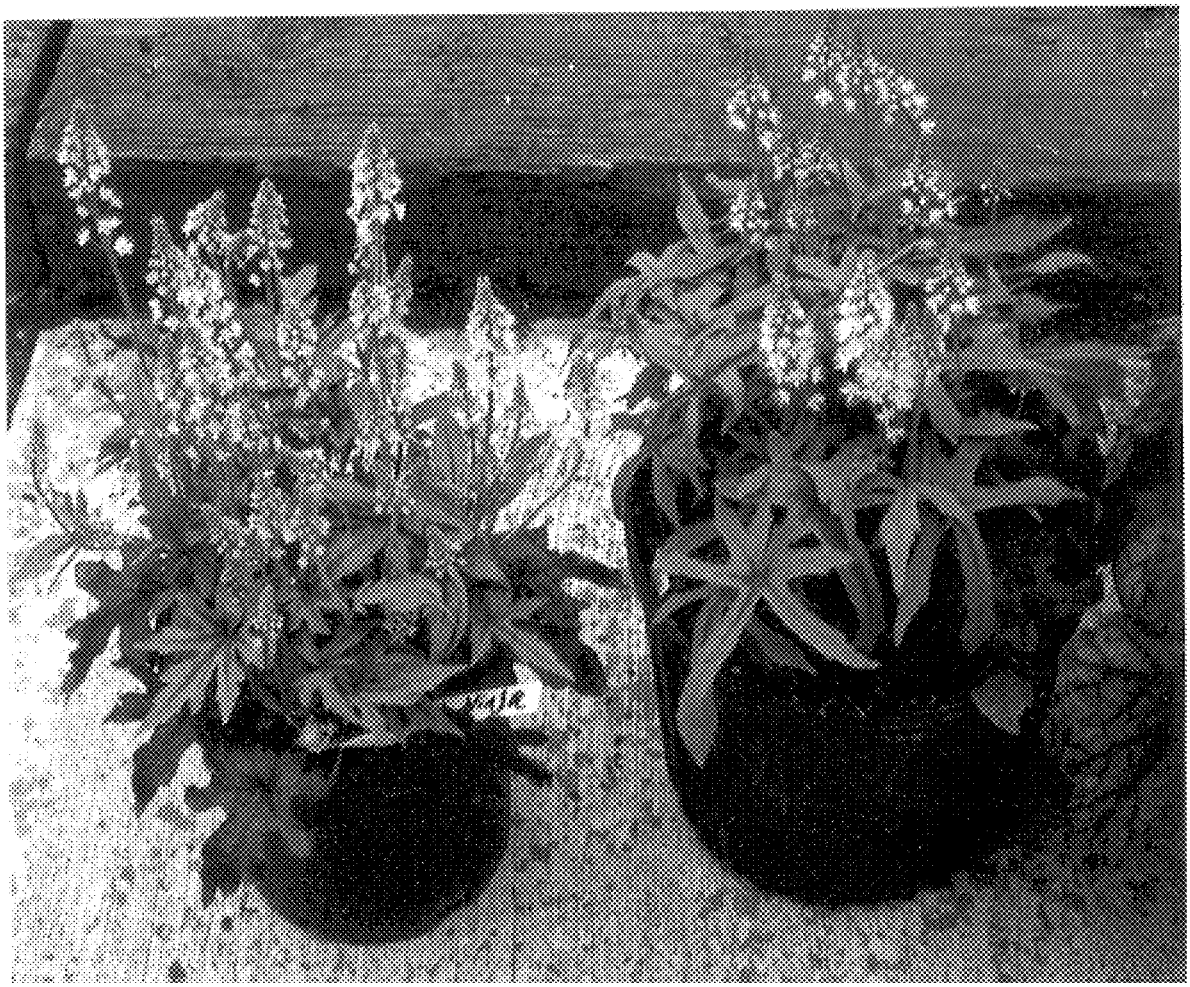

FIG. 2 is a picture of T. 'Ninja' (subject of U.S. Plant Patent Application Ser. No. 08/982,243) next to T. 'Cygnet' for comparison.

Tiarella 'Ninja' is to the left and marked with a white label.

DETAILED PLANT DESCRIPTION

The following is a detailed description of the new Tiarella hybrid based on observations of specimens in Canby, Oreg. The color descriptions are all based on The Royal Horticultural Society Colour Chart and The American Rhododendron Society publication: *A CONTRIBUTION TOWARD STANDARDIZATION OF COLOR NAMES IN HORTICULTURE.*

Foliage:

*Type.*—Evergreen herbaceous in a hard winter.

*Shape.*—Palmate, deeply 7-lobed, irregularly toothed; central lobe elongated, tapers to a fine point from a narrow base; lobe tip\finely incised.

*Length.*—6.5–10.5 cm.

*Width.*—7–10.5 cm.

*Petiole length.*—varies 10–20 cm.

*Margins.*—Incised.

*Apex.*—Rostratus (terminating gradually in a long point).

*Base.*—Sagittate, slightly imbricate.

*Texture.*—Slightly rugose, velvet-matte finish.

*Leaf arrangement.*—Basal clump.

*Venation.*—Reticulate.

Flower:

*Petal count.*—5 petals. 5 calyx lobes.

*Petal shape.*—Triangular, clawed.

*Flower type.*—Complete, calyx tube campanulate, ovary superior.

*Flower size.*—0.80 cm.

*Flower number.*—40–55 blooms per raceme.

*Blooming habit.*—Simple upright raceme to 30 cm. 30–35 racemes per second year plant.

*Bloom period.*—May to June. Minor sporadic rebloom in summer and fall.

*Fragrance.*—Lightly fragrant.

Color Characteristics

Foliage: Leaves have a sharply contrasting black blotch along each lobe's central vein and the leaf center (Summer through Winter: R.H.S. 202A Black Group; Spring: R.H.S. 200A Brown Group).

Color:

*Spring/Summer upper surface.*—R.H.S. 137B Green Group (Moderate Olive Green ARS).

*Spring/Summer new growth and flower stems.*—R.H.S. 184B Greyed Purple Group (Moderate Red ARS).

Flowers: White, shading to pink; pink would be as R.H.S. 36B Red Purple Group. (Light Yellowish Pink ARS).

Average height: 47 cm.

Habit: This cultivar is not rhizomatous.

Disease resistance: None observed.

DESCRIPTION OF PARENT PLANTS

This Tiarella hybrid has characteristics which make it unique from its parents: a well-marked selection of *Tiarella wherryi* and *Tiarella cordifolia* 'Dunvegan'. *Tiarella wherryi* is described in Hortus Third as " . . . having more slender racemes and narrower petals" (than *Tiarella cordifolia* and *Tiarella cordifolia* 'Dunvegan'). *Tiarella cordifolia*, which is described in *Hortus Third* as having leaves "ovate or cordate to 4" long, flowers whitish or reddish." The *Tiarella cordifolia* cultivar 'Dunvegan' has deeply lobed leaves with no contrasting central patch. Unlike its parents, Tiarella 'Cygnet' has no rhizomes, has deeply cut, highly colored leaves with an extremely elongated central lobe, and a heavier blooming habit.

I claim:

1. A new and distinct hybrid of Tiarella plant substantially as shown and described, characterized by unique, heavily lobed leaves of marked coloration.

* * * * *